United States Patent [19]

Wortrich

[11] Patent Number: 4,750,643
[45] Date of Patent: Jun. 14, 1988

[54] STERILE FLUID DISPENSING SYSTEM AND METHOD

[75] Inventor: Theodore S. Wortrich, Mission Viejo, Calif.

[73] Assignee: Sugrin Surgical Instrumentation, Inc., Placentia, Calif.

[21] Appl. No.: 892,811

[22] Filed: Aug. 4, 1986

[51] Int. Cl.⁴ .......................... B67B 7/24; B67D 3/00; A61M 5/14; A61M 5/245
[52] U.S. Cl. ..................... 222/81; 222/482; 604/80; 604/244; 604/411
[58] Field of Search ............ 604/80, 81, 173, 411–414, 604/256, 905, 258, 283, 284, 244, 251, 252; 222/81, 481, 481.5, 83, 83.5, 482

[56] References Cited

U.S. PATENT DOCUMENTS

| | | | |
|---|---|---|---|
| 1,236,865 | 3/1917 | Pittenger | 604/258 |
| 3,841,334 | 10/1974 | Wolf | 604/173 X |
| 3,941,126 | 3/1976 | Dietrich et al. | 222/81 X |
| 4,392,851 | 7/1983 | Elias | 604/414 X |
| 4,439,183 | 3/1984 | Theeuwes | 604/251 X |

Primary Examiner—H. Grant Skaggs
Assistant Examiner—Lisa C. Waag
Attorney, Agent, or Firm—Bogucki, Scherlacher, Mok & Roth

[57] ABSTRACT

A disposable system for enabling a succession of individuals to be supplied with a sterile medical solution during operative and other procedures utilizes a number of spaced apart, penetrable elastomerically sealed funnels branching from an outlet from the solution container or an attached drip chamber. A standard sterile administration set having a spike end may be inserted into the seal of a first funnel to provide flow to a first individual. After the first procedure is completed the conduit to the first funnel is clamped off and the sequence repeated, but with the spike end of a second administration set inserted for supply to solution to a second individual. This sequence may be repeated for a selectable number of branches, enabling valuable solution from a container to be used with minimum wastage but without danger of cross-contamination.

10 Claims, 2 Drawing Sheets

STERILE FLUID DISPENSING SYSTEM AND METHOD

BACKGROUND OF THE INVENTION

1. Field of the Invention

This invention relates to a system and method for economically transferring a sterile fluid from an enclosed single source in a sterile environment to multiple recipients in successive fashion. More particularly, this invention relates to a low cost, disposable transfer system and method that allows a single reservoir to provide a relatively high flow rate of sterile fluid into several independent paths without danger of cross-contamination between any of the recipients, but with efficient use of the fluid.

2. Description of the Prior Art

Many medical and biologically compatible solutions for human and animal use are supplied in closed sterile containers having fixed volumes (e.g. 500 cc of saline or other isotonic solution). The solution is expensive because of the biologic and sterility requirements that must be met. In a typical widely used surgical procedure in opthalmology, for example, a system is employed in which the eye is irrigated and occasionally aspirated as required. Irrigation is accomplished by feeding the chosen sterile solution into the eye by an implanted or attached device at a controlled rate using a flow control device such as a drip regulating chamber. By far the most widely used system is based on the use of a sterile container having a puncturable elastomeric seal and a disposable administration set having a spike ended conduit at one end, an integral drip chamber, and a needle, catheter or other delivery device at the other end of a flexible tubing. The spike, which is sterile, is used to penetrate into the container through the seal. Since the flow rate can be substantial the size of the conduit must be of moderate size (e.g. $\frac{1}{8}''$ inner diameter) to allow for unrestricted flow under gravity feed conditions. The administration sets are commercially available products having a number of different forms. Because of cost, ease of use, and reliability this system of spiking into an elastomeric seal is used in the great majority of administration sets. Medical practitioners and hospitals maintain a large inventory of such sets and prefer to use the seal/spike approach for cost and convenience reasons.

While these types of transfer systems maintain the fluid in a sterile condition from the supply container to the individual, they are often quite costly to use because with present devices much of the solution is often wasted. Once the seal is punctured and the spike is removed the seal is no longer sterile. Of the 500 cc in a standard container, for example, only about 20-30% is typically employed in a routine cataract removal, for example. Thus, when the operation is complete, the remainder of the bottle is discarded. Furthermore, using smaller fixed volumes (e.g. 250 cc) of solutions is not cost efficient since they are disproportionately priced in comparison to the larger volumes (e.g. 500 cc), and it is not practical to carry a large inventory of different sized containers or to use very small containers in series.

There are certain known types of connector systems than can fully utilize the sterile solution of a container by enabling successive connection to different individuals. These systems employ a special manifold having multiple ports, each including a special connector and a control valve. Additional tubing sets can be attached if they have special mating connectors. However, the tubing sets then are available only for use in this type of system. Such coupling systems are impractical and too expensive for many applications, because of the cost of the special connectors and attachments.

There is an economic need to utilize all of the sterile solution which is stored in a punctured container. The desired system and method should be able to maintain a high flow rate of the solution, yet yield multiple independent pathways. The independent pathways should be designed so that when one pathway has been used it may be closed off without affecting the sterile condition of the adjacent pathways. The system and method should also allow for multiple withdrawals from the solution without a decrease in flow rate using standard sized medical attachments or the like.

SUMMARY OF THE INVENTION

Systems and methods in accordance with the invention employ a container having a sterile solution and transfer means that can be attached to the container so as to deliver the solution at a high flow rate to successive multiple users employing standard medical instruments without the need for special fittings, the fear of cross-contamination or waste of the valuable sterile solution.

In accordance with one aspect of the invention, the spike end of a set including a drip chamber device is inserted into the elastomeric seal of a container for a suitable sterile biological solution, the output end being coupled to a multi-branch flow divider. Separate flow paths from each branch of the divider include delivery funnels having sterile elastomeric seal faces. These seals can be separately punctured by spike-ended devices on commercial administration sets for delivery of solution serially to different users, as previously used tubing lines are clamped off. The contents of a supply container can thus be efficiently used without introducing a significant cost increase in the delivery system.

In a more specific example, a 15 drop drip chamber includes a 1.2 micron hydrophobic filter that is integrally attached to the chamber and acts to stabilize flow rate in the drip chamber by permitting air ingress while blocking fluid passage. The other axial end of the drip chamber connects to a multiple branch coupler having more than one branch, up to a maximum of eleven. Attached to the distal ends of the branch coupler are individual lines of flexible tubing whose opposite ends each terminate at a different specially formed delivery funnel having a transverse puncturable elastomeric seal. The puncture site is sealed in a sterilized manner with a protective ring which is crimped around the outside of the delivery funnel. A plastic divider around the necks of the delivery funnel keeps them separate and apart, holding them in convenient position for use and avoiding any possibility of cross-contamination from contact. A clamp is placed on each flexible tubing length between the branch coupler and the delivery funnel, so that after one branch line has been used it is closed and reverse flow is blocked. This prevents any cross-contamination by transfer of fluid between separate lines and keeps the remaining lines available for use.

BRIEF DESCRIPTION OF THE DRAWINGS

A better understanding of the invention may be had by reference to the following description, taken in conjunction with the accompanying drawings, in which.

DETAILED DESCRIPTION OF THE INVENTION

Figure 1:
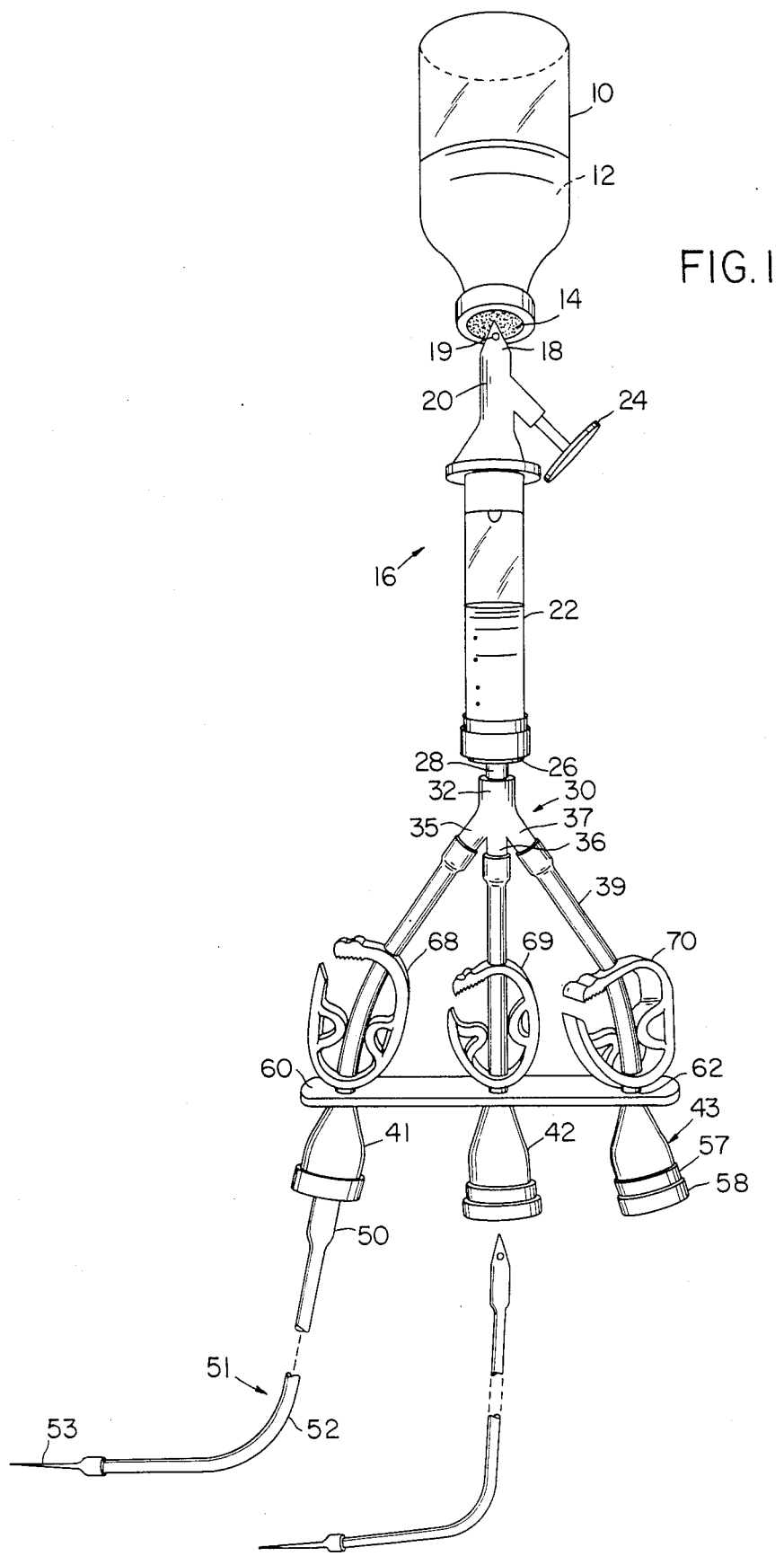
FIG. 1 is a perspective view of a system in accordance with the invention, showing one administration set in position with another ready for use.
Figure 2:
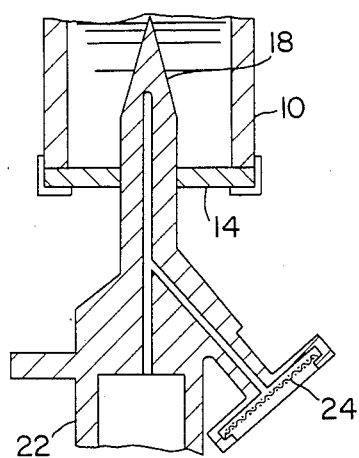
FIG. 2 is a side sectional view of a portion of the system of FIG. 1, showing further details of a puncture spike and drip chamber relative to a supply container.
Figure 3:
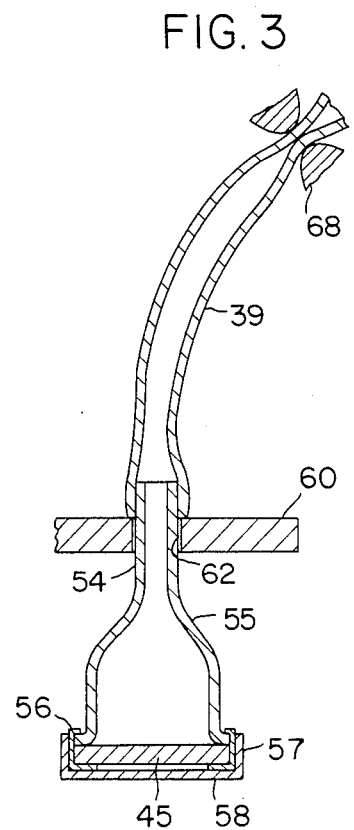
FIG. 3 is a side sectional view of a different part of the system showing further details of a delivery funnel, clamp, funnel divider and a second puncture spike.

In accordance with the invention, a closed container 10 of valuable biologic fluid 12 is shown as disposed in a typical surgical situation, inverted for gravity feed down to the operative sets (holding means have not been shown inasmuch as any conventional retainer may be used). The container 10 has a puncturable elastomeric seal 14 at its otherwise open end, transverse to the opening. The seal 14 is originally enclosed by a sterilized protective covering (not shown) that is removable to maintain the seal 14 and fluid in a sterile condition. The seal 14 is of substantial diameter, e.g. greater than 1 2/2". When fluid is desired for a therapeutic or operative purpose the protective covering around the puncturable seal 14 is removed and a dispensing device 16 is attached. The device 16 includes at one end, in this example, a standard sized sterile medical spike 18 which is inserted into the puncturable seal 14 of the container 10. The puncture spike 18 has a tapered tip with surface apertures 19 that extend into communication with a central conduit (not shown in detail) in a cylindrical body 20. The cylindrical body 20 forms the upper end of an integrally attached fifteen drop drip chamber 22 of somewhat flexible material. A second portion of the cylindrical body 20 branches out at an angle in relation to the spike 18 to receive an internal 1.2 micron hydrophobic disk filter 24 that is open to the environment at one side and in communication with the interior of the container 10 and the drip chamber 22 on the other. Bacteria and other contaminants are blocked by the filter 24, although air passes inwardly as the hydrostatic head in container 10 and chamber 22 are lowered. Sterile fluid cannot pass the hydrophobic barrier, and in consequence the flow rate is stabilized.

The drip chamber 22 is an elongated cylinder of conventional design whose distal end is enclosed by an integral cap 26 having a vertically extending hollow output stub 28 in its center. A sterile flow divider comprising a multi-branch coupler 30 has an integral inlet tube 32 coupled to the output stub 28 of the drip chamber 22 and, in this example, three branch outlet conduits 35, 36, 37 on the distal end. There may be at least two and up to a maximum of eleven outlet conduits that branch out from the body of the coupler 30. Attached to each of the branch conduits 35, 36, 37 is a length of flexible (here PVC) tubing 39. The opposite end of each conduit 35, 36, 37 receives the small end of specially formed diverging delivery funnel 41, 42 or 43. Each delivery funnel 41, 42, 43, here of resilient plastic, includes an elastomeric transverse end seal 45 that functions as a puncturable surface for insertion of a standard size puncture spike 50 forming a part of a commercial administration set 51. The administration set 51 typically includes a suitable length of flexible tubing 52 leading to a needle 53 or other element such as a catheter. A separate drip chamber (not shown) is often included in this type of set. The delivery funnel 41–43 has a narrow elongated neck 54 inserted within the tubing 39 and integral with a diverging body 55 which terminates in a concentric mouth having an outer lip 56 around its periphery. The funnel lip 56 acts as a base to securely hold the sterile rubber end seal 45 in transverse position. A flange ring 57 is crimped about the lip 56 of the delivery funnel 41, 42 or 43. A sterile cover 58 is secured over the wide end of the funnel and the outer part of the end seal 45 to maintain the puncture site area in a sterile condition until it is to be used.

The funnels 41–43 are kept in alignment and physically separate by a plastic divider 60 consisting of an integral length of plastic having a plurality of regularly spaced apart surface openings 62. The openings 62 are spaced apart sufficiently to keep the funnels 41–43 separated for easy spike insertion. This also insures that the puncture site of one delivery funnel, e.g. 42, does not communicate with the puncture site of the surrounding delivery funnels, e.g. 41, 43. The number of openings 62 in each plastic divider 60 corresponds to the number of delivery funnels 41–43 being used. The plastic divider 60 is disposed with a snug fit around the neck 54 of a delivery funnel, e.g. 41, so that substantial movement and slippage are eliminated.

A different spring clamp 68, 69, 70 is mounted on each length of tubing 39 between the corresponding branch conduit and respective delivery funnel. The spring clamps, when engaged, close off the flow of fluid from the respective branch conduits 35–37 so that the contents of the container 10 may be delivered to other individuals without the fear of cross-contamination.

The administration sets 51 are sterile, commonly used units having flow openings suitable for relatively high flow rates. The sterile fluid dispensing system of this invention represents a substantial improvement over previous dispensing systems. A number of persons can be served from a single container, the contents of which are thus most efficiently used.

In using the system of this invention a user removes the sterile cover (not shown) from the elastomeric seal 14 of the fluid source container 10, before inserting the sterile puncture spike 18. The puncture spike 18 is forced into the center of the elastomeric seal 14, maintaining the system biologically closed unless the spike 18 is removed. The flexible sides of the drip chamber 22 can then be squeezed to adjust the level. The fluid container 10 may be inverted and placed in position before or after the level adjustment is made. The sterile covering 58 that is held over each delivery funnel 41–43 is now removed from one funnel, e.g. 41. The chosen delivery funnel 41 is held for insertion of the standard size, sterilized puncture spike 50 of an administration set 51 into the center of the rubber end seal 45. The fluid level in the drip chamber 22 can be adjusted by applying pressure to the flexible sides of the chamber 22.

This then enables delivery to the patient or other recipient of the needed amount of fluid 12, typically substantially less than the contents of the container 10. When the procedure is complete for that individual, the clamp, e.g. clamp 68, is closed onto the tubing 39. When a need arises for delivery of fluid to a different individual, the protective sterile covering 58 over the second delivery funnel 42 is removed and the face of the rubber end seal 45 is exposed. The rubber end seal 45 is then penetrated with a second puncture spike 50. Then the drip chamber 22 is squeezed and released for level adjustment. When the recipient's need for fluid 12 is met, the tubing 39, corresponding to the second delivery funnel 42, is closed with another clamp 69. The same process may be repeated for a third recipient, in this example, insuring maximum use of fluid from the container 10.

The system and method of this invention deliver a valuable sterile fluid at a high flow rate to multiple recipients by making it possible to use at least two and up to a maximum of eleven administration sets. Each administration set is insertable into a corresponding delivery funnel and may be closed off with a clamp so that the delivery funnel can be punctured by a standard size medical spike for a first use and later clamped off when this use has ceased. When a need arises for the delivery of the fluid to another patient, the next corresponding delivery funnel is spiked for use, with the prior spike then being removed. This process of spiking and clamping successive delivery funnels in administration sets may be repeated a number of times to deliver sterile fluids at a high flow rate to the recipients without cross-contamination.

Where many administration sets (say eleven) are to be used, the delivery funnels are preferably arranged in a circular pattern for best compactness and accessibility.

Since further changes and modifications of the invention will occur to and can be made readily by those skilled in the art without departing from the inventive concept, the invention is not to be taken as limited except by the scope of the appended claims.

What is claimed is:

1. The method of supplying a fluid under sterile conditions from a closed container to each of two or more recipients using puncturable seals without danger of cross-contamination or the need for special attachments comprising the steps of:
    providing a principal flow from the sterilized closed container;
    providing a succession of individual branch flow paths which are closed off with puncturable seals;
    puncturing one of the puncturable seals to deliver fluid to a user;
    closing off the branch flow path before the punctured seal after an appropriate amount of fluid has been delivered; and
    repeating the sequence with a different branch flow path so that the single sterilized source can be used to supply more than one individual without danger of cross-contamination.

2. A system for dispensing a quantity of fluid from a sterile source sequentially to a number of users, each under sterile conditions, comprising:
    a closed container of sterile fluid the container having a penetrable elastomeric seal which may be punctured once by a spike ended sterile conduct member;
    first spike ended conduit means inserted through the seal to provide a sterile outlet for the fluid;
    a sterile branch flow coupler attached to the first conduit means and having at least first and second resilient branch conduits extending therefrom;
    at least one sterile puncturable branch seal means coupler to each of the different conduits at an opposite end from the branch flow coupler;
    at least two sterile output spike ended conduit means, each insertable in a different one of the branch seal means for providing output flow to an associated flow device;
    at least one clamp mounted on each branch conduit for closing off the conduit after dispensing fluid therefrom to isolate the outlet of the conduit from a later used different branch conduit, whereby the contents of the closed container may be delivered under sterile conditions to more than one individual to utilize as much as feasible of a standard fluid volume without the danger of cross contamination between individuals;
    each associated branch seal means comprising a plurality of hollow funnel members, each having a first open end defined by a small width neck, a diverging body, and a distal second open end defining an open mouth, and having a peripheral lip surrounding the second open end of the housing;
    said open mouth defining a receptacle for the associated branch seal means, said seal means having a diameter sufficient to receive a spike, and a solid but penetrable elastomeric material such as rubber; and
    the system further comprising a removable plastic covering that is seated around the lip of the second open end of the housing.

3. A system for providing a plurality of individually usable, non-cross-contaminating outlets for a sterile fluid comprising:
    means providing a principal flow path;
    branching means coupled to the fluid flow path for providing at least two branch paths;
    a separate delivery funnel coupled to each of the branch paths, each of the delivery funnels comprising a neck portion coupled to the branch path, a flexible diverging body and an open mouth end;
    means for sealing the open mouth end of each of the delivery funnels comprising a transverse puncturable elastomeric seal; and
    divider means coupled to each of the delivery funnels in the neck regions thereof for maintaining the funnel accessible but separate.

4. A reusable dispensing sterile transfer system for channeling fluids from a sterilized source to another source so that the source may be more fully utilized, comprising:
    a drip chamber, said chamber having a first end and a second distal end and a hollow interior that allows for a regulated fluid flow inside the chamber;
    a sterilized hollow spike, said spike having an upper tip portion with an aperture, a body having an axial portion and an integral slanted portion and means providing internal communication between the end of the slanted portion and the axial portion communicating with the tip portion of the spike, the body of the spike having a distal end opposite the tip portion, said distal end of the body communicating with and terminating inside the first end of the drip chamber in a sealing manner;
    multi-channel flow means having a main body with a hollow interior which branches off into a plurality of elongated parts, the main body sealingly communicating with the distal end of the drip chamber;
    a number of housing means, each having a first open end and a second open end, said first open end having a smaller diameter than the second open end, the first open end communicating with a different one of the elongated parts via a coupling, and the second open end terminating in a horizontal lip;

each of the housing means having a solid but penetrable seal means defining a puncture site, said seal means being disposed across the second open end of the housing means, said seal means providing a secure sterilized seal inside the second open end of the housing;

each of the housing means having removable sterilized cover means enclosing the second end of the housing means and sealing the puncture site until removed;

a plurality of hollow administration set means corresponding to the number of multi-channel flow means, each administration set means having a first end and including a spike inserted in a different seal means and a second end including means for delivery to an individual who is to use the fluid; and clamp means to releasably close the coupling at a point between the flow means and the housing means.

5. The device in claim 4 including separator means having a plurality of spaced apertures corresponding to the number of elongated parts, said separator means receiving a portion of a different one of the housing means in each of the spaced apertures to keep the housing means separated, and maintaining the sites from cross-contamination.

6. The device of claim 4 wherein the spike includes a hydrophobic filter which stabilizes the flow rate of the fluid into the drip chamber.

7. The device of claim 4 wherein the flow means include a plurality fo lengths of flexible synthetic tubing forming the coupling between the first open end of each housing means and the elongated parts.

8. The device of claim 4 wherein the puncture site consists of a rubber stopper fitting across the second open end of the housing means.

9. The device of claim 4 where the seal means consists of a plastic cap that is attached to the horizontal lip of the housing means.

10. The device of claim 8 wherein the housing means defines a funnel shape with the first open end being an elongated circular neck, a diverging portion integral to the circular neck extends downward away from the first open end toward the second open end, the diverging portion terminating in a concentric portion of the housing, said concentric portion extends from the termination of the diverging portion to the second open end to define a seat for the rubber stopper.

* * * * *

UNITED STATES PATENT AND TRADEMARK OFFICE
CERTIFICATE OF CORRECTION

PATENT NO. : 4,750,643
DATED : June 14, 1988
INVENTOR(S) : Theodore S. Wortrich

It is certified that error appears in the above-identified patent and that said Letters Patent is hereby corrected as shown below:

Title page:

after "[73] Assignee:", "Sugrin" should read --Surgin--. Column 5, line 52, after "conditions" and before the comma (",") insert --and each without loss of sterile conditions--; line 53, after "fluid" and before "the" insert a comma --,--. Column 6, line 9, after "individuals" change the semicolon (";") to a period --.--.
Column 8, line 7, after "plurality" and before "lengths", "fo" should read --of--.

Signed and Sealed this

Twenty-second Day of August, 1989

Attest:

DONALD J. QUIGG

*Attesting Officer*  *Commissioner of Patents and Trademarks*